United States Patent [19]

Gsell

[11] Patent Number: 4,918,086

[45] Date of Patent: Apr. 17, 1990

[54] 1-NITRO-2,2-DIAMINOETHYLENE DERIVATIVES

[75] Inventor: Laurenz Gsell, Basel, Switzerland

[73] Assignee: Ciba-Geigy Corporation, Ardsley, N.Y.

[21] Appl. No.: 224,623

[22] Filed: Jul. 27, 1988

[30] Foreign Application Priority Data

Aug. 7, 1987 [CH] Switzerland .......................... 3051/87
Mar. 9, 1988 [CH] Switzerland ............................ 888/88

[51] Int. Cl.$^4$ .................... C07D 213/26; A61K 31/44
[52] U.S. Cl. ...................................... 514/351; 514/344; 514/346; 514/352; 514/355; 514/356; 514/347; 514/332; 514/343; 514/255; 546/264; 546/265; 546/332; 546/281; 546/261; 546/286; 546/287; 546/288; 546/289; 544/360; 544/365
[58] Field of Search ............... 546/264, 265, 332, 281, 546/261, 286, 287, 288, 289; 544/360, 365; 514/344, 346, 351, 352, 355, 356, 347, 332, 343, 255

[56] References Cited

U.S. PATENT DOCUMENTS

| | | | |
|---|---|---|---|
| 4,028,375 | 6/1977 | Krenzer .............................. | 548/137 |
| 4,567,188 | 1/1986 | Niemers et al. ..................... | 514/332 |
| 4,625,025 | 11/1986 | Iwata .................................... | 544/53 |
| 4,647,570 | 3/1987 | Shiokawa et al. .................. | 514/341 |
| 4,680,294 | 7/1987 | Shiokawa et al. .................. | 514/256 |
| 4,742,060 | 5/1988 | Shiokawa et al. .................. | 514/252 |

FOREIGN PATENT DOCUMENTS 302389 2/1989 European Pat. Off. .

OTHER PUBLICATIONS

Gazetta Chimica Italiana III, pp. 217–222 (1981).
Arch. Pharm. (Weinheim), 319, p. 160–167 (1986).
Advances in Pesticide Science—Part 2 (1978), pp. 206–217.

Primary Examiner—Jane T. Fan
Attorney, Agent, or Firm—Kevin T. Mansfield

[57] ABSTRACT

There are disclosed novel 1-nitro-2,2-diaminoethylene derivatives of formula I

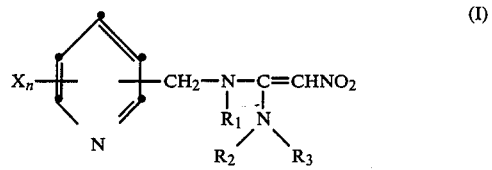

wherein
X is chlorine, fluorine, unsubstituted or halogen-substituted $C_1$–$C_5$alkyl; unsubstituted or halogen-substituted $C_1$–$C_5$alkoxy, unsubstituted or halogen-substituted $C_1$–$C_5$akylthio, unsubstituted or halogen-substituted alkylsulfinyl, unsubstituted or halogen-substituted alkylsulfonyl; or also nitro, cyano, thiocyanato, $C_3$–$C_5$haloalkenyl, $C_3$–$C_5$haloalkynyl, hydroxy, $C_1$–$C_5$alkoxycarbonyl, amino, $C_1$–$C_4$dialkylamino, $C_1$–$C_5$alkylcarbonyl, $C_1$–$C_5$alkylcarbamoyl or $C_1$–$C_5$alkylcarbonyloxy,
n is an integer from 0 to 4,
$R_1$ is hydrogen, $C_1$–$C_5$alkyl or $C_3$–$C_7$cycloalkyl,
$R_2$ is hydrogen, $C_1$–$C_5$alkyl, $C_3$–$C_7$cycloalkyl,
$R_3$ is hydrogen, $C_1$–$C_5$alkyl, $C_3$–$C_7$cycloalkyl, benzyl or pyridinylmethyl, or $R_2$ and $R_3$, together with the linking nitrogen atom, are the pyrrolidinyl or piperazinyl radical,
with the proviso that not more than one of the substituents $R_1$, $R_2$ and $R_3$ is hydrogen, and the cis and trans-isomers and salts thereof. The invention also relates to the preparation of these novel compounds and to compositions containing them and to the use thereof in pest control, especially for controlling insects.

21 Claims, No Drawings

1-NITRO-2,2-DIAMINOETHYLENE DERIVATIVES

The present invention relates to novel 1-nitro-2,2-diaminoethylene derivatives, to the preparation of these compounds and to intermediates for their synthesis. The invention further relates to pesticidal compositions which contain the novel compounds and to the use thereof in pest control.

Specifically, the present invention relates to 1-nitro-2,2-diaminoethylene derivatives of formula I

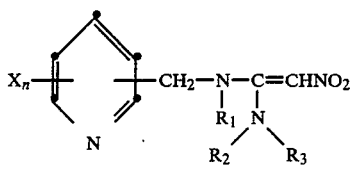

wherein
X is chlorine, fluorine, unsubstituted or halogen-substituted $C_1$–$C_5$alkyl; unsubstituted or halogen-substituted $C_1$–$C_5$alkoxy, unsubstituted or halogen-substituted $C_1$–$C_5$akylthio, unsubstituted or halogen-substituted alkylsulfinyl, unsubstituted or halogen-substituted alkylsulfonyl; or also nitro, cyano, thiocyanato, $C_3$–$C_5$haloalkenyl, $C_3$–$C_5$haloalkynyl, hydroxy, $C_1$–$C_5$alkoxycarbonyl, amino, $C_1$–$C_4$dialkylamino, $C_1$–$C_5$alkylcarbonyl, $C_1$–$C_5$alkylcarbamoyl or $C_1$–$C_5$alkylcarbonyloxy, n is an integer from 0 to 4, $R_1$ is hydrogen, $C_1$–$C_5$alkyl or $C_3$–$C_7$cycloalkyl, $R_2$ is hydrogen, $C_1$–$C_5$alkyl, $C_3$–$C_7$cycloalkyl, $R_3$ is hydrogen, $C_1$–$C_5$alkyl, $C_3$–$C_7$cycloalkyl, benzyl or pyridinylmethyl, or $R_2$ and $R_3$, together with the linking nitrogen atom, are the pyrrolidinyl or piperazinyl radical, with the proviso that not more than one of the substituents $R_1$, $R_2$ and $R_3$ is hydrogen, and to the cis- and trans-isomers and the salts of compounds of formula I.

The alkyl radicals by themselves or as moieties of other radicals, for example alkoxy, alkylthio, alkylsulfinyl or alkylsulfonyl, can be straight chain or branched. Examples of such alkyl groups are methyl, ethyl, propyl, cyclopropyl, isopropyl, butyl, isobutyl, sec-butyl, tert-buyl or pentyl and the isomers thereof.

Halogen is, for example, fluorine and chlorine as well as bromine and iodine. Fluorine and chlorine are preferred.

The halogen-substituted $C_1$–$C_5$alkyl groups can be straight chain or branched and be only partially halogenated or perhalogenated, the same definitions applying to the halogens and to the alkyl moieties as indicated above. Suitable examples of such substituents are methyl which is substituted by one to three fluorine, chlorine and/or bromine atoms, for example $CHF_2$ or $CF_3$; ethyl which is substituted by one to five fluorine, chlorine and/or bromine atoms, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is substituted by one to seven fluorine, chlorine and/or bromine atoms, for example $CH_2CHBrCH_2Br$, $CF_2CHFCF_3$, $CH_2CF_2CF_3$ or $CH(CF_3)_2$; butyl or an isomer thereof which is substituted by one to nine fluorine, chlorine and/or bromine atoms, for example $CF(CF_3)CHFCF_3$ or $CH_2(CF_2)_2CF_3$.

A suitable pyridinylmethyl radical in the compounds of formula I is each of the α-, β- and γ-isomers of formulae:

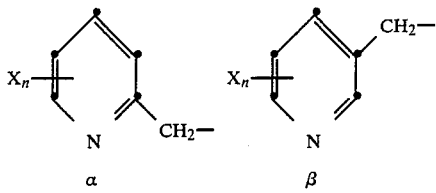

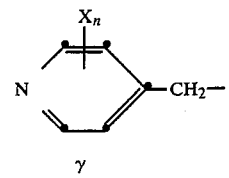

Depending on the steric arrangement of the substituents attached to the ethylene carbon atoms, the compounds of formula I are obtained in the form of one of the cis- or trans-isomers or as a mixture thereof.

If one of the substituents $R_1$, $R_2$ and $R_3$ is hydrogen, the enamines of this invention can also be in the tautomeric imine form.

The compounds of formula I can also be obtained in the form of acid addition salts. Suitable acids for forming such salts are organic and inorganic acids, for example: hydrochloric acid, hydrobromic acid, nitric acid, different phosphoric acids, sulfuric acid, acetic acid, propionic acid, butyric acid, valeric acid, oxalic acid, malonic acid, maleic acid, fumaric acid, lactic acid, tartaric acid or salicylic acid.

Within the scope of this invention, the following groups of compounds of formula I are preferred:

1. Those 1-nitro-2,2-diaminoethylene derivatives in which X is chlorine or fluorine.

2. Those 1-nitro-2,2-diaminoethylene derivatives in which
   X is chlorine,
   n is 0 to 2,
   $R_1$ is hydrogen, methyl, ethyl or cyclopropyl,
   $R_2$ is hydrogen or methyl,
   $R_3$ is hydrogen, $C_1$–$C_5$alkyl, benzyl or pyridinylmethyl, or $R_2$ and $R_3$, together with the linking nitrogen atom, are the pyrrolidinyl or piperazinyl radical.

2.1 Among these compounds, those compounds of formula Ia

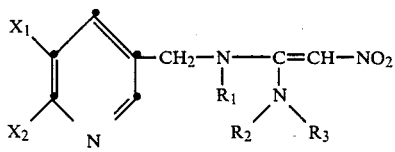

are preferred, wherein $X_1$ and $X_2$ are each independently of the other hydrogen or chlorine and $R_1$ is hydrogen, methyl or ethyl.

2.1.1 Among this group of compounds, those compounds are preferred in which n is 0.

Among this last mentioned group of compounds, the following individual compounds are preferred:

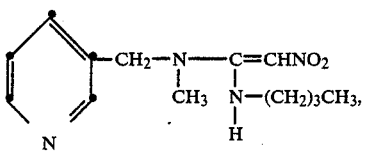

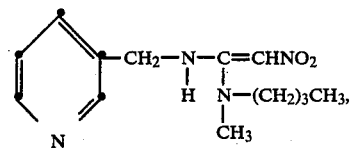

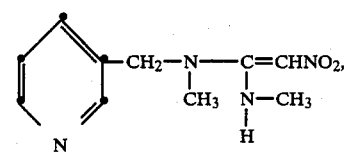

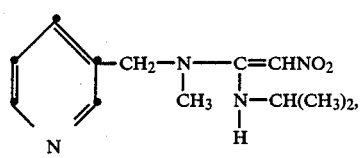

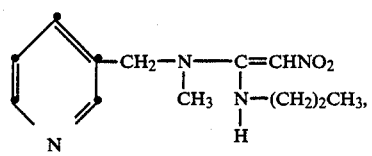

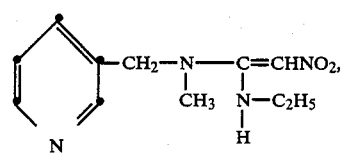

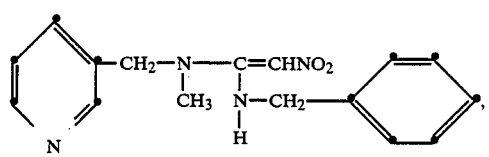

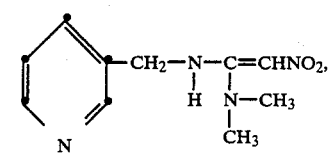

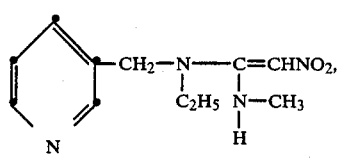

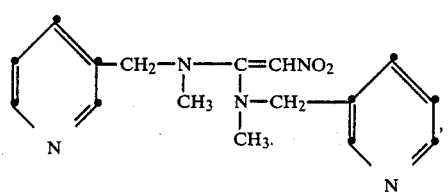

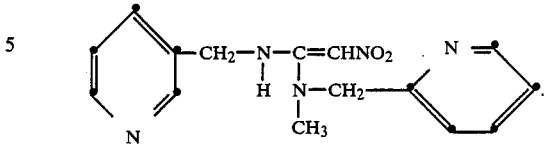

2.1.2 Further preferred compounds of formula Ia as defined in 2.1 are those wherein $X_1$ and $X_2$ are chlorine.

Among this group of compounds, the compound of formula

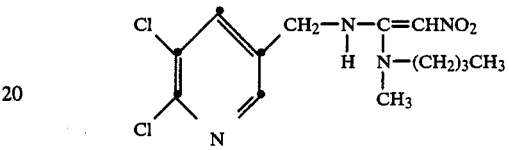

is particularly preferred.

Finally, among the compounds defined in group 2 above, the compounds of formula Ic

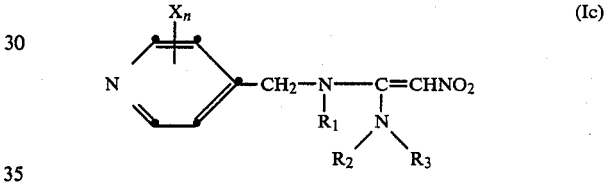 (Ic)

are preferred.

The compounds of formula I can be prepared by stepwise reaction of the nitromethylene derivatives of formula II

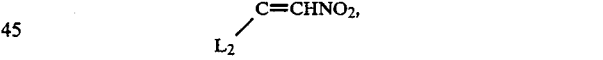 (II)

wherein $L_1$ and $L_2$ are leaving groups such as alkylthio, alkylsulfinyl or chlorine, with suitably substituted amines.

This process comprises reacting the compound of formula II, wherein $L_1$ and $L_2$ are as defined above, either (a) first with the equivalent amount of a pyridinylmethylamine of formula III

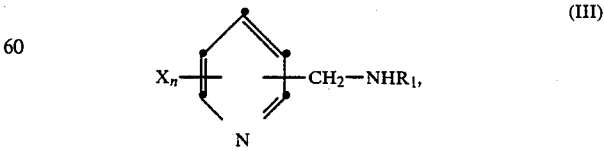 (III)

wherein $R_1$ is as defined for formula I, to give the 1-nitro-2-pyridinylmethylaminoethylene derivative of formula IV

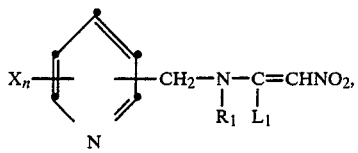

wherein $R_1$, X, n and $L_1$ are as defined for formulae I and II respectively, and subsequently reacting said compound of formula IV with an amine of formula V

wherein $R_2$ and $R_3$ are as defined for formula I, to give the 1-nitro-2,2-diaminoethylene derivative of formula I; or (b) reacting a nitroethylene derivative of formula II first with the equivalent amount of an amine of formula V to give the 1-nitro-2-aminoethylene derivative of formula VI

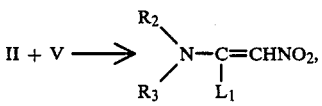

wherein $R_2$, $R_3$ and $L_1$ are as defined for formula II and V respectively, and then reacting said compound of formula VI with a pyridinylmethylamine of formula III to give the 1-nitro-2,2-diaminoethylene derivative of formula I, and isolating said derivative.

In a preferred embodiment of the preparatory process, the respective intermediate of formula IV or VI is further processed without being isolated.

The intermediates of formula IV are novel, have pronounced insecticidal properties, and likewise constitute an object of the present invention. The compounds of formula IV can be prepared in the first step of the above described process and then isolated as such.

The present invention also relates to the process for the preparation of the compounds of formula I via the novel intermediates of formula IV, likewise to the process via the known intermediates of formula VI to give the compounds of formula I, as well as to the process for the preparation of the compounds of formula IV.

Suitable solvents for the preparation of the intermediates IV and VI as well as the final products of formula I are aprotic polar solvents such as acetonitrile, dimethyl formamide, dimethyl sulfoxide and the like; and also aromatic solvents such as benzene or toluene, as well as chlorinated hydrocarbons, tetrahydrofuran, or ethers and alcohols.

The reactions are carried out in the temperature range from 0° to the boiling point of the reaction mixture, under atmospheric or, in some cases, reduced pressure.

The addition of a salt which acts as buffer, for example disodium hydrogen phosphate, can favourably influence the reaction course.

The starting materials of formula II are known and, like the intermediates of formula VI, can be prepared by known methods.

Those compounds of formula II, wherein $L_1$ and $L_2$ are lower alkylthio or benzylthio, are known intermediates of preparative organic chemistry and are commercially available.

Those compounds of formula II, wherein $L_1$ and $L_2$ are chlorine, can be prepared from the known 1-nitro-2-trichloroethane by dehydrochlorination in accordance with European patent application No. A-135 803.

Those compounds of formula II, wherein $L_1$ is an alkylthio group and $L_2$ is an alkylsulfinyl group, are described in U.S. patent specification No. 4 028 375.

The intermediates of formula VI and their preparation are described in Gazetta Chimica Italiana 111, 217 (1981) and in Arch. Pharm. (2), 161–167 (1986).

The compounds of formula

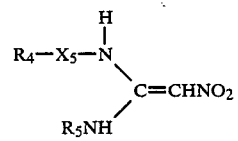

wherein
$R_4$ is an unsubstituted or substituted aryl or heteroaryl radical,
$R_5$ is a straight chain, branched or cyclic alkyl or alkenyl group which may be substituted by alkoxy or cycloalkyl, or is an unsubstituted or substituted aryl or heteroaryl radical, and
$X_5$ is unsubstituted or alkyl-substituted methylene or a chemical bond,
with the proviso that $R_5$ is not aryl if $X_5$ is a single bond, are disclosed as cardiovascular drugs, in particular vasodepressive drugs, in German Offenlegungsschrift No. 3 232 462.

1-Pyridinylalkyl-2-nitromethylidene-1,3-diazacycloalkanes having insecticidal, miticidal and nematicidal properties, and wherein the heterocycle has 5 to 7 members, are disclosed in European patent application No. A-154 178. This publication relates to compounds of formula

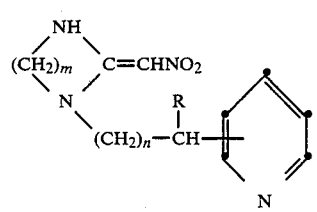

wherein
m is 2, 3 or 4, and
n is 0, 1, 2 or 3.

Similar insecticidally active 1-pyridinylmethyl-2-nitromethylidene-azacycloalkanes and 1-pyridinylmethyl-2-nitromethylidene-1,3-diazacycloalkanes are also disclosed in European patent application No. A-192 060.

In contradistinction to the compounds disclosed in the aforementioned publications, wherein the ethylene carbon atom in 2-position is defined as member of a heterocycle, the corresponding radical of the compounds of this invention is not cyclic.

Other insecticidally active nitroethylene derivatives are known from "Advances in Pesticide Science", Part 2, Pergamon Press, 1979, pp. 206.271. These compounds, however, do not contain a pyridinylmethyl radical.

It is the object of the present invention to provide further compounds for pest control.

Surprisingly, it has been found that the compounds of formula I of this invention and the intermediates of formula IV are effective pesticides while being well tolerated by warm-blooded animals and plants. The compounds of formulae I and IV are therefore suitable e.g. for controlling pests of animals and plants. Such pests belong principally to the phylum of Arthropoda, such as in particular insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, e.g. mites and ticks. Every development stage of the pests can be controlled, i.e. the adults, pupae and nymphs, and also in particular the larvae and eggs. It is thus possible to control effectively in particular larvae and eggs of phytopathogenic insect pests and mites in crops of ornamentals and useful plants, e.g. in fruit and vegetable crops, and especially in cotton crops. If compounds of formulae I and IV are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the main targeted pests are ectoparasites, such as mites and ticks and Diptera, for example Lucilia sericata.

The good pesticidal activity of the compounds of formulae I and IV corresponds to a mortality of at least 50-60% of the above pests.

The compounds of formulae I and IV are used in unmodified form, or preferably together with the inert, agriculturally acceptable adjuvants conventionally employed in the art of formulation, and can therefore be formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I and/or IV or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I or IV to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or IV or a combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

1. Preparation of the intermediates and final products
   1.1 Intermediates of formula IV Example 1.1.1:

Preparation of 2-(N-methyl-N-pyridin-3-ylmethylamino)-2-methylthio-1-nitroethylene

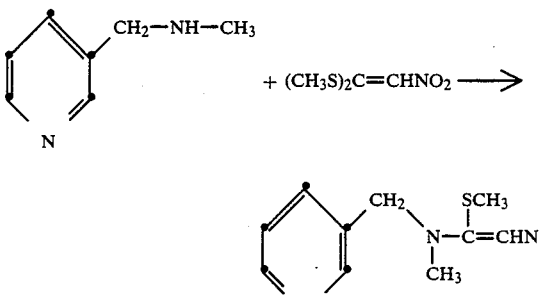

26 g (0.156 mol) of 1-nitro-2,2-dimethylthioethylene are dissolved in 80 ml of toluene and 18.3 g (0.15 mol) of N-methyl-N-pyridin-3-ylmethylamine are added dropwise to this solution at 70° C. over 30 minutes. The reaction solution is stirred for 1 hour at the same temperature.

After evaporation of the solvent, the residue is purified by column chromatography using silica gel with a 97:3 mixture of ethyl acetate/methanol as eluant. The solvent is removed by evaporation under vacuum, affording 2-(N-methyl-N-pyridin-3-ylmethylamino)-2-methylthio-1-nitroethylene in the form of a viscous oil (see Compound 1.1, Table 1).

The following compounds can be prepared in corresponding manner:

TABLE 1

$$Y-N-C=CHNO_2$$
with $R_1$ above N and $L_2$ below N

| Compound | Y | $L_2$ | $R_1$ | phys. data |
|---|---|---|---|---|
| 1.1 | pyridin-3-yl-CH$_2$— | CH$_3$S— | CH$_3$— | viscous oil |
| 1.2 | pyridin-2-yl-CH$_2$— | CH$_3$S— | H— | m.p. 136–138° C. |
| 1.3 | pyridin-3-yl-CH$_2$— | CH$_3$S— | H— | m.p. 124–126° C. |

Example 1.2.1:

Preparation of 2-(N-butyl-N-methylamino)-2-methylthio-1-nitroethylene

A solution of 8.26 g (0.05 mol) of 1-nitro-2,2-di(methylthio)ethylene and 5.25 g (0.06 mol) of N-n-butyl-N-methylamine in toluene is refluxed for 2 hours. After evaporation of the toluene under vacuum, 10.2 g of 2-(N-butyl-N-methylamino)-2-methylthio-1-nitroethylene are isolated as an oil ($n_D^{21}$ = 1.584). (Compound 2.1, Table 2).

The following compound can be prepared in corresponding manner:

TABLE 2

$$L_2-C=CHNO_2$$
with N below bearing $R_2$ and $R_3$

| Compound | $L_2$ | $R_1$ | $R_3$ | phys. data |
|---|---|---|---|---|
| 2.1 | CH$_3$S— | CH$_3$— | n-C$_4$H$_9$— | $n_D^{21}$ = 1.584 |

1.3 Final products Example 1.3.1:

Preparation of 2-butylamino-2-(N-methyl-N-pyridin-3-ylmethylamino)-1-nitroethylene

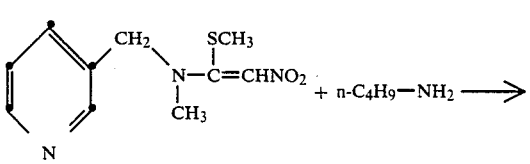

-continued

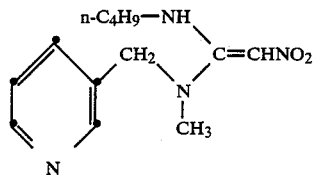

6 g of 2-(N-methyl-N-pyridin-3-ylmethylamino)-2-methylthio-1-nitroethylene and 2.19 g of n-butylamine in 20 ml of acetonitrile as solvent are kept for 4 hours at 70° C. After evaporation of the solvent under vacuum, the residue is dissolved in dichloromethane and the solution is chromatographed through a column of silica gel with a 95/5 mixture of dichloromethane/methanol as eluant. The solvent is removed by evaporation, affording 2-butylamino-2-(N-methyl-N-pyridin-3-ylmethylamino)-1-nitro-ethylene as an oil ($n_D^{22}=1.618$). (Compound 3.1, Table 3).

Example 1.3.2:

Preparation of 2-(N-n-butyl-N-methylamino)-2-(pyridin-3-ylmethylamino)-1-nitroethylene A mixture of 5.2 g of 2-(N-n-butyl-N-methylamino)-2-methylthio-1-nitroethylene, 2.84 g of pyridin-3-ylmethylamine and 3.69 g of disodium hydrogen phosphate in 30 ml of ethanol is refluxed for 1 hour. After removing the salt by filtration, the solvent is evaporated from the solution under vacuum and the residue is chromatographed through a column of silica gel with a 95/5 mixture of ethyl acetate/methanol. The product is eluated with ethylacetate/methanol (85/15). The solvent is removed by evaporation, affording 3.7 g of 2-(N-n-butyl-N-methylamino)-2-(pyridin-3-ylmethylamino)-1-nitroethylene as a viscous oil (Compound 3.2, Table 3).

The NMR spectrum and the elemental analysis are consistent with the structural formula.

Example 1.3.3:

Preparation of 2-methylamino-2-(N-methyl-N-pyridin-3-yl-methylamino)-1-nitroethylene A mixture of 5.0 g of 2-(N-methyl-N-pyridin-3-ylmethylamino)-2-methylthio-1-nitroethylene, 2.07 g of a 33% solution of methylamine in ethanol, 3.12 g of disodium hydrogenphosphate and 25 ml of ethanol is refluxed for 1 hour. The salts are removed by filtration and the filtrate is concentrated by evaporation under vacuum. The residue is chromatographed through a column of silica gel with a 95/5 to 85/5 mixture of ethyl acetate/methanol as eluant. After evaporation of the solvent, the product is isolated as a viscous oil (Compound 3.3, Table 3).

The following compounds are prepared in corresponding manner:

TABLE 3

$$Y-N-C=CHNO_2$$
with $R_1$ on N and $N(R_2)(R_3)$

| Comp. | Y | $R_1$ | $R_2$ | $R_3$ | phys. data |
|---|---|---|---|---|---|
| 3.1 | Z* | CH₃— | H— | n-C₄H₉— | $n_D^{22}$: 1.618 |
| 3.2 | Z* | H— | CH₃ | n-C₄H₉— | viscous oil |
| 3.3 | Z* | CH₃— | H— | CH₃ | viscous oil |
| 3.4 | Z* | CH₃— | H— | (CH₃)₂CH— | m.p. 103–113° C. |
| 3.5 | Z* | CH₃— | H— | n-C₃H₇— | viscous oil |
| 3.6 | Z* | CH₃— | H— | C₂H₅— | oil |
| 3.7 | Z* | CH₃— | H— | C₆H₅CH₂— | m.p. 100.5–102° C. |
| 3.8 | Z* | CH₃— | CH₃— | Z* | viscous oil |
| 3.9 | Z* | H— | —(CH₂)₄— | | solid |
| 3.10 | Z* | H— | —(CH₂)₅— | | viscous oil |
| 3.11 | Z* | H— | CH₃— | CH₃— | viscous oil |
| 3.12 | Z* | H— | CH₃— | n-C₄H₉ | viscous oil |
| 3.13 | (3-chloropyridin-2-yl)methyl | H— | CH₃— | n-C₄H₉— | |
| 3.14 | (2,3-dichloropyridin-5-yl)methyl | H— | CH₃— | n-C₄H₉— | |
| 3.15 | Z* | H— | CH₃— | (pyridin-2-yl)methyl | |
| 3.16 | Z* | CH₃CH₂— | H— | n-C₄H₉— | resin |

TABLE 3-continued $$Y-N(R_1)-C(=CHNO_2)-N(R_2)(R_3)$$

| Comp. | Y | $R_1$ | $R_2$ | $R_3$ | phys. data |
|---|---|---|---|---|---|
| 3.17 | Z* | 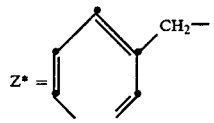 | H— | $CH_3$— | 114–116° C. |
| 3.18 | Z* | 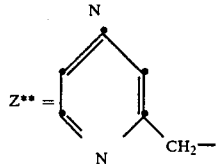 | H— | $n-C_4H_9$— | $n_D^{24}$: 1.6040 |
| 3.19 | Z* | 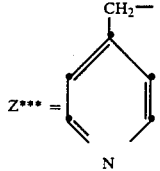 | H— | $n-C_6H_5CH_2$— | $n_D^{24}$: 1.6258 |
| 3.20 | Z* | $CH_3CH_2$— | H— | Z* | resin |
| 3.21 | Z* | $n-C_4H_9$— | H— | $CH_3$— | resin |
| 3.22 | Z* | $CH_3CH_2$— | H— | $CH_3$— | resin |
| 3.23 | Z*** | $n-C_3H_7$— | H— | $CH_3$— | resin |
| 3.24 | Z*** | $CH_3$— | H— | $CH_3$— | resin |
| 3.25 | Z*** | $n-C_4H_9$ | H— | $n-C_3H_7$— | resin |
| 3.26 | Z** | $CH_3$— | H— | $n-C_4H_7$— | resin |

Z* = 4-pyridylmethyl (CH₂ at 4-position)

Z** = 3-pyridylmethyl

Z*** = 2-pyridylmethyl

Example 2:

Formulations of compounds of formulae I and IV according to Preparatory Examples 1.1.1 and 1.3.1 to 1.3.3 (throughout, percentages are by weight)

| 2.1. Emulsifiable concentrates | (a) | (b) |
|---|---|---|
| a compound according to Preparatory Examples 1.1.1 and 1.3.1 to 1.3.3 | 10% | 25% |
| calcium dodecylbenzenesulfonate | — | 5% |
| castor oil polyethylene glycol ether (36 mol of ethylene oxide) | 25% | 5% |
| tributylphenol polyethylene glycol ether (30 mol of ethylene oxide) | — | — |
| cyclohexanone | — | 40% |
| butanol | 15% | — |
| xylene mixture | — | 25% |
| ethyl acetate | 50% | — |

Emulsions of any required concentration can be produced from such concentrates by dilution with water.

| 2.2. Solutions | (a) | (b) |
|---|---|---|
| a compound according to Preparatory Examples 1.1.1 and 1.3.1 to 1.3.3 | 10% | 5% |
| polyethylene glycol 400 | 70% | — |
| N-methyl-2-pyrrolidone | 20% | 20% |
| epoxidised coconut oil | — | 1% |
| petroleum distillate (boiling range 160–190° C.) | — | 74% |

These solutions are suitable for application in the form of microdrops.

| 2.3. Granulates | (a) | (b) |
|---|---|---|
| a compound according to Preparatory Examples 1.1.1 and 1.3.1 to 1.3.3 | 5% | 10% |
| kaolin | 94% | — |

-continued

| 2.3. Granulates | (a) | (b) |
|---|---|---|
| highly dispersed silicic acid | 1% | — |
| attapulgite | — | 90% |

The active ingredient or ingredients is or are dissolved in methylene chloride, the solution is sprayed onto the carrier, and the solvent is subsequently evaporated off in vacuo.

| 2.4. Extruder granulate | |
|---|---|
| a compound according to Preparatory Examples 1.1.1 and 1.3.1 to 1.3.3 | 10% |
| sodium lignosulfonate | 2% |
| carboxymethylcellulose | 1% |
| kaolin | 87% |

The active ingredient or ingredients is or are mixed and ground with the adjuvants, and the mixture is subsequently moistened with water. The mixture is extruded and then dried in a stream of air.

| 2.5. Coated granulate | |
|---|---|
| a compound according to Preparatory Examples 1.1.1 and 1.3.1 to 1.3.3 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | (a) | (b) | (c) | (d) |
|---|---|---|---|---|
| a compound according to Preparatory Examples 1.1.1 and 1.3.1 to 1.3.3 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and, optionally, grinding the mixture in a suitable mill.

| 2.7. Wettable powders | (a) | (b) | (c) |
|---|---|---|---|
| a compound according to Preparatory Examples 1.1.1 and 1.3.1 to 1.3.3 | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| 2.8. Suspension concentrate | |
|---|---|
| a compound according to Preparatory Examples 1.1.1 and 1.3.1 to 1.3.3 | 40% |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Example 3.1:

Stomach toxicant and contact action against Laodelphax striatellus and Nilaparvata lugens (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an aqueous emulsion formulation prepared from the emulsifiable concentrate of Example 2a) and containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

In this test, the compounds 1.1, 3.1, 3.2, 3.3., 3.4, 3.5, 3.6, 3.7 and 3.8 effect 80–100% kill of Nilaparvata lugens.

Example 3.2:

Systemic action against Nilaparvata lugens (water)

Rice plants which are about 10 days old and about 10 cm high are put into a plastic beaker which contains 20 ml of an aqueous emulsion formulation prepared from the emulsifiable concentrate of Example 2a) and containing the test compound in a concentration of 100 ppm and which is sealed with a perforated plastic lid. The root of each rice plant is pushed through a hole in the plastic lid into the aqueous test formulation. The hole is then plugged with cotton wool to fix the plant and to exclude any contact with the gas phase of the test formulation. The rice plant is then populated with 20 nymphs of Nilaparvata lugens in the $N_2$ to $N_3$ stage and covered with a plastic cylinder. The test is carried out at 26° C. and 60% relative humidity and the plant is exposed to light for 16 hours. A mortality count is made 5 days later using untreated controls for comparison purposes, thereby establishing whether the test compound absorbed through the root kills the test organisms on the upper parts of the plant.

In this test compounds 1.1, 3.1, 3.2, 3.3, 3.4, 3.5, 3.6, 3.7 and 3.8 effect 80–100% kill of Nilaparvata lugens.

Example 3.3:

Action against Spodoptera littoralis (larvae):

Two cotton plants each having a height of about 15–20 cm and grown in pots are treated with a sprayable liquid preparation of the test compound. After the spray coating has dried, the potted plants are placed in a metal container having a capacity of about 20 liters and covered with a glass plate. The humidity in the interior of the covered container is regulated such that no water of condensation forms. Direct light falling on the plants is avoided. The three plants are then infested altogether with:

(a) 50 larvae of Spodoptera littoralis in the $L_1$-stage;
(b) 20 larvae of Spodoptera littoralis in the $L_3$-stage.

Evaluation in comparison with untreated controls is made after 2 days, taking into account the number of still living larvae.

Compound 3.3 effects 80–100% kill at a concentration of 400 ppm.

Example 3.4:

Action against Heliothis virescens (eggs):

A cotton plant having a height of about 15–20 cm and grown in a pot is treated with a sprayable liquid preparation of the test compound. After the spray coating has dried, the potted plant is placed in a metal container having a capacity of about 20 liters and covered with a glass plate. The humidity in the interior of the covered container is regulated such that no water of condensation forms. Direct light falling on the plant is avoided. The plant is then infested altogether with 2 egg deposits of Heliothis virescens. (The procedure is that two leaves of each plant are put into a plexiglass cylinder sealed at both ends with gauze. Part of a cotton leaf with egg deposits of Heliothis deposited thereon is added to the leaves sealed in the cylinder.)

Evaluation in comparison with untreated controls is made after 4 days, taking into account the hatching rate (number of larvae hatched from the eggs).

Compound 3.3 and 3.6 effect 100% kill at a concentration of 400 ppm in this test.

Example 3.5:

Contact action against Myzus persicae 4- to 5-day old pea seedlings (Pisum sativum) which have been reared in water are each populated with about 200 aphids of the species Myzus persicae before the start of the test. The treated plants are sprayed direct to drip point 24 hours later with an aqueous suspension containing the test compound in a concentration of up to 200 ppm. Two plants are used for each compound at its given concentration. An evaluation of percentage mortality is made 24 and 72 hours respectively after application. The test is carried out at 21–22° C. and about 60% relative humidity.

Compounds 1.1, 3.1, 3.2, 3.3, 3.4, 3.5, 3.6, 3.7 and 3.8 exhibit good activity in this test.

Example 3.6:

Contact action against Aphis craccivora

Before the start of the test, 4- to 5-day old pea seedlings (Pisum sativum) reared in pots are each populated with about 200 insects of the species Aphis craccivora. The treated plants are sprayed direct to drip point 24 hours later with an aqueous formulation containing the test compound. Two plants are used for each test compound at its given concentration. A mortality count is made after 24 and 72 hours respectively. The test is carried out at 21°–22° C. and at a relative humidity of about 55%.

Compounds 1.1, 3.1, 3.2, 3.3, 3.4, 3.5, 3.6, 3.7 and 3.8 exhibit good activity in this test.

Example 3.7:

Action against soil insects (Diabrotica balteata)

5 maize seedlings about 1 to 3 cm in length and a disc of filter paper are immersed in an aqueous formulation containing 400 ppm of the test compound. The moist filter paper disc is placed at the bottom of a 200 ml plastic beaker, and then the 5 treated maize seedlings together with 10 larvae of diabrotica balteata in the second to third larval stage are placed in the beaker. Two tests are carried out for each test compound at its given concentration. The beakers containing the larvae are kept for 6 days at daylight, a relative humidity of 40 to 60% and at temperature of 22° to 24° C. The percentage kill of the test insects is then determined.

Compounds 1.1, 3.1, 3.2, 3.3, 3.4, 3.5, 3.6, 3.7 and 3.8 exhibit good activity in this test.

Example 3.8:

Insecticidal systemic action against Aphis craccivora

Bean plants which have grown roots are transplanted into pots containing 60 ccm of soil. Then 50 ml of an aqueous formulation (prepared from a 25% wettable powder) of the respective test compound in a concentration of 400 ppm are poured direct onto the soil in the pots.

After 24 hours the parts of the treated plants above the soil are populated with aphids of the species Aphis craccivora and plastic cylinders are then slipped over the plants to protect the aphids from any possible contact with the test substance either directly or via the gas phase.

The evaluation of percentage mortality is made 48 and 72 hours after the start of the test. Two plants, each in a separate pot, are used for each test substance at its given concentration. The test is carried out at about 25° C. and 60% relative humidity.

Compounds 1.1, 3.1, 3.2, 3.3, 3.4, 3.5, 3.6, 3.7 and 3.8 exhibit good activity in this test.

Example 3.9:

Insecticidal systemic action against Myzus persicae

Cabbage plants which have grown roots are transplanted in the 4- to 5-leaf stage into pots containing 60 ccm of soil. Then 50 ml of an aqueous formulation (prepared from a 25% wettable powder) of the respective test compound in a concentration of 400 ppm are poured direct onto the soil.

After 24 hours the parts of the treated plants above the soil are populated with aphids of the species Myzus persicae and plastic cylinders are then slipped over the plants to protect the aphids from any possible contact with the test substance either directly or via the gas phase.

The evaluation of percentage mortality is made 48 hours after the start of the test. Two plants, each in a separate pot, are used for each test substance at its given concentration. The test is carried out at about 25° C. and 60% relative humidity.

Compounds 1.1, 3.1, 3.2, 3.3, 3.4, 3.5, 3.6, 3.7 and 3.8 exhibit good activity in the test.

Example 10:

Leaf penetration action against Aphis craccivora

A small shoot of Vicia faba, which is highly infested with aphids of the species Aphis craccivora, is placed in each of a number of 8 cm high plastic beakers (diameter about 6 cm). Each beaker is covered with a plastic lid having a punched opening of 2 cm diameter in the centre. A leaf of a Vicia faba-plant is then placed over the opening in the lid without separating this leaf from the potted plant. The leaf is then fixed on the beaker with a second punched lid above the opening of the first lid. From underneath, i.e. through the opening of the first lid, the aphids in the beaker then infect the leaf of the plant used as bait. An aqueous formulation of the test compound is then applied in a concentration of 400 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds 1.1, 3.1, 3.2, 3.3, 3.4, 3.5, 3.6, 3.7 and 3.8 exhibit good activity in this test.

Example 11:

Systemic action against Aphis craccivora (in water)

Pea seedlings about 1 to 2 cm in height which had been infested with a population of the aphids 24 hours before the beginning of the test are placed in 20 ml of an aqueous mixture containing the test compound in a concentration of 400 ppm. The aqueous mixture is prepared from an emulsifiable concentrate or a wettable powder formulation of the test compound and is contained in a vessel which is closed with a perforated plastic lid. The roots of each of the infested pea plantlets are pushed through a hole in the plastic lid into the mixture containing the test substance. Each hole is then sealed with cotton wool to fix the plant and to prevent the aphids from being affected by the test substance via the gas phase.

The test is carried out at 20° C. and at 60% relative humidity. After two days an evaluation is made of the number of test organisms which are no longer capable of sucking as compared with untreated controls, thereby establishing whether the test substance absorbed via the roots kills the aphids at the upper parts of the plants.

In this test, compounds 1.1, 3.1, 3.2, 3.3, 3.4, 3.5, 3.6, 3.7 and 3.8 have a good systemic action against insects of the species Aphis craccivora.

Example 12:

Action against Nephotettix cincticeps (nymphs)

The test is carried out with growing plants. For this purpose approximately twenty-day-old rice plants about 15 cm in height are planted into each of a number of pots (diameter: 5.5 cm).

The plants in each pot are sprayed on a rotary table with 100 ml of an acetonic solution containing 400 ppm of the test compound. After the spray coating has dried, each plant is populated with 20 nymphs of the test organisms in the second or third stage. To prevent the cicadas from escaping, a plexiglass cylinder is slipped over each of the plants and sealed with a gauze top. The nymphs are kept for 5 days on the treated plants, which have to be watered again at least once. The test is carried out at a temperature of about 23° C. and at 55% relative humidity. The plants are exposed to light for 16 hours.

Compounds 1.1, 3.1, 3.2, 3.3, 3.4, 3.5, 3.6, 3.7 and 3.8 exhibit good activity in this test.

What is claimed is:

1. A 1-nitro-2,2-diaminoethylene derivative of formula I

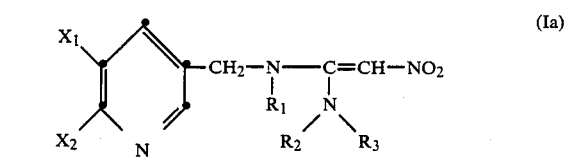

wherein

X is chlorine, fluorine, unsubstituted or halogen-substituted $C_1$-$C_5$alkyl; unsubstituted or halogen-substituted $C_1$-$C_5$alkoxy, unsubstituted or halogen-substituted $C_1$-$C_5$akylthio, unsubstituted or halogen-substituted alkylsulfinyl, unsubstituted or halogen-substituted alkylsulfonyl; or also nitro, cyano, thiocyanato, $C_3$-$C_5$haloalkenyl, $C_3$-$C_5$haloalkynyl, hydroxy, $C_1$-$C_5$alkoxycarbonyl, amino, $C_1$-$C_4$dialkylamino, $C_1$-$C_5$alkylcarbonyl, $C_1$-$C_5$alkylcarbamoyl or $C_1$-$C_5$alkylcarbonyloxy, n is an integer from 0 to 4, $R_1$ is hydrogen, $C_1$-$C_5$alkyl or $C_3$-$C_7$cycloalkyl, $R_2$ is hydrogen, $C_1$-$C_5$alkyl, $C_3$-$C_7$cycloalkyl, $R_3$ is hydrogen, $C_1$-$C_5$alkyl, $C_3$-$C_7$cycloalkyl, benzyl or pyridinylmethyl, or $R_2$ and $R_3$, together with the linking nitrogen atom, are the pyrrolidinyl or piperazinyl radical, with the proviso that not more than one of the substituents $R_1$, $R_2$ and $R_3$ is hydrogen, or a cis- or trans-isomer or a salt thereof.

2. A compound according to claim 1, wherein X is chlorine or fluorine.

3. A compound according to claim 2, wherein

X is chlorine, n is 0 to 2, $R_1$ is hydrogen, methyl, ethyl or cyclopropyl, $R_2$ is hydrogen or methyl, $R_3$ is hydrogen, $C_1$-$C_5$alkyl, benzyl or pyridinylmethyl, or $R_2$ and $R_3$, together with the linking nitrogen atom, are the pyrrolidinyl or piperazinyl radical.

4. A compound according to claim 3 of formula Ia

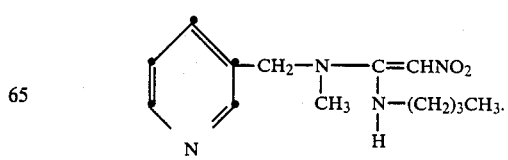

wherein $X_1$ and $X_2$ are hydrogen or chlorine and $R_1$ is hydrogen, methyl or ethyl.

5. A compound according to claim 4, wherein n is 0.

6. A compound according to claim 4 of formula Ia, wherein $X_1$ and $X_2$ are chlorine.

7. The compound according to claim 5 of formula

8. The compound according to claim 5 of formula

[pyridine]-CH$_2$-NH-C(=CHNO$_2$)-N(CH$_3$)-(CH$_2$)$_3$CH$_3$.

9. The compound according to claim 5 of formula

[pyridine]-CH$_2$-N(CH$_3$)-C(=CHNO$_2$)-NH-CH$_3$.

10. The compound according to claim 5 of formula

[pyridine]-CH$_2$-N(CH$_3$)-C(=CHNO$_2$)-NH-CH(CH$_3$)$_2$.

11. The compound according to claim 5 of formula

[pyridine]-CH$_2$-N(CH$_3$)-C(=CHNO$_2$)-NH-(CH$_2$)$_2$CH$_3$.

12. The compound according to claim 5 of formula

[pyridine]-CH$_2$-N(CH$_3$)-C(=CHNO$_2$)-NH-C$_2$H$_5$.

13. The compound according to claim 5 of formula

[pyridine]-CH$_2$-N(CH$_3$)-C(=CHNO$_2$)-NH-CH$_2$-[phenyl].

14. The compound according to claim 5 of formula

[pyridine]-CH$_2$-NH-C(=CHNO$_2$)-N(CH$_3$)-CH$_3$.

15. The compound according to claim 5 of formula

[pyridine]-CH$_2$-N(CH$_3$)-C(=CHNO$_2$)-N(CH$_3$)-CH$_2$-[pyridine].

16. The compound according to claim 5 of formula

[pyridine]-CH$_2$-NH-C(=CHNO$_2$)-N(CH$_3$)-CH$_2$-[pyrrole/pyridine].

17. The compound according to claim 5 of formula

[pyridine]-CH$_2$-N(C$_2$H$_5$)-C(=CHNO$_2$)-NH-CH$_3$.

18. The compound according to claim 6 of formula

[3,4-dichloropyridine]-CH$_2$-NH-C(=CHNO$_2$)-N(CH$_3$)-(CH$_2$)$_3$CH$_3$.

19. A compound according to claim 3 of formula $$\text{[X}_n\text{-pyridine]}-CH_2-N(R_1)-C(=CHNO_2)-N(R_2)(R_3) \quad (Ic)$$

20. A pesticidal composition which comprises an effective amount of a compound of formula I as claimed in claim 1, together with an inert carrier.

21. A method of controlling pests of animals and plants, which comprises contacting said pests in their development stages with a pesticidally effective amount of a compound of formula I as claimed in claim 1.

* * * * *